United States Patent [19]

Gallot et al.

[11] Patent Number: 4,859,753

[45] Date of Patent: Aug. 22, 1989

[54] BRANCHED LIPOPEPTIDE POLYMERS FORMING THERMOTROPIC AND LYOTROPIC LIQUID CRYSTALS, THEIR APPLICATIONS AND CORRESPONDING MONOMERS

[75] Inventors: Bernard Gallot; André Douy, both of Olivet, France

[73] Assignee: Centre Natioonal de la Recherche Scientifique (CNRS), Paris, France

[21] Appl. No.: 884,751

[22] Filed: Jul. 11, 1986

[30] Foreign Application Priority Data

Jul. 19, 1985 [FR] France ................ 85 11121

[51] Int. Cl.$^4$ ............................ C08H 1/00
[52] U.S. Cl. .................... 526/238.1; 252/299.01; 252/315.1
[58] Field of Search ........... 526/238.1; 252/315.1, 252/299.01

[56] References Cited

U.S. PATENT DOCUMENTS 4,600,526  7/1986  Gallot et al. ................ 252/299.01

FOREIGN PATENT DOCUMENTS 0105777  4/1986  European Pat. Off.

OTHER PUBLICATIONS

Werner, Chem. Abstr., vol. 97, No. 23, 192611x, Dec. 6, 1982.
Garg, Chem. Abstr., vol. 73, No. 23, 116276f, Dec. 7, 1970.
Czarniecka, "Polypeptide Liquid Crystals: A Deuterium NMR Study," Mol. Cryst. Liq. Cryst. vol. 63, pp. 205–214, 1981.
Shibaer et al., "Thermotropic . . . Polymers with Amino Acid Fragments in the Side Chains," J. Polymer Sci., vol. 17, no. 6, pp. 1671–1684, 1982.

Primary Examiner—John F. Terapane
Assistant Examiner—John M. Covert
Attorney, Agent, or Firm—Griffin, Branigan & Butler

[57] ABSTRACT

Branched polymers resulting from homopolymerization or copolymerization of monomers of formula I:

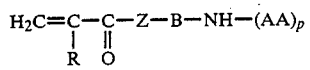

R is H or a lower alkyl group of $C_1$ to $C_3$; Z is O or NH; B has the formula:

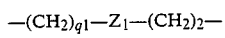

in which $q_1$ and $q_2$ are integers greater than or equal to 1, the sum of which is less than approximately 32 and $Z_1$ represents a single bond or O, S, NH, CO or CO—NH; $(AA)_p$ represents a peptide radical comprising p linked aliphatic alpha-aminoacids, bound at B by its carboxyl group, each amino acid comprising less than 15 carbon atoms and being possibly substituted at one carbon atom of the chain by a carboxylic acid or ester, amide or amine group, the terminal amine group of the peptide radical being possibly acylated by a R'CO group, R' being an alkyl radical comprising 1 to 4 carbon atoms, or by any other group stable under the conditions of synthesis; and p represents a number ranging between 1 and 200.

Application as thermotropic and lyotropic liquid crystals and emulsifying and foaming agents.

8 Claims, No Drawings

BRANCHED LIPOPEPTIDE POLYMERS FORMING THERMOTROPIC AND LYOTROPIC LIQUID CRYSTALS, THEIR APPLICATIONS AND CORRESPONDING MONOMERS

FIELD OF THE INVENTION

The present invention relates to branched polymers based on lipopeptides, which are in a mesomorphic state at ambient temperature, as well as their applications and the monomers used for their preparation.

In the terms of the present description, "branched polymers based on lipopeptides" is taken to mean polymers comprising pendant lipopeptide chains, polymers also known as "comb polymers".

The present invention also relates, when the branched polymers are amphipathic, to their applications as emulsifying and foaming agents.

A certain number of polymers have already been described which have liquid crystal properties and result from the binding of mesogenic groups to the polymers chain by the intermediate of a flexible spacer arm. These polymers present the properties of low-molecular weight liquid crystals with the qualities of polymers, and are of great technical interest.

Reference could be made, for example, to the book "Polymer liquid crystals" edited by A. Ciferri, W. R. Krigbaum and R. B. Meyer and published by Academic Press in 1982. In particular, it is possible to cite all the optoelectronic screen display systems or temperature-dependent displays.

The present invention relates to new polymers which are in a mesomorphic state above room temperature and present successively two types of phase: smectic and nematic, before giving an isotropic liquid phase at a markedly higher temperature. Now, it is particularly desirable, for display applications, to have only mesophases which are stable over a large temperature range.

In addition, and this is really unexpected, they are thermotropic and lyotropic at one and the same time, that is to say that the phase change can be observed either by increasing the temperature of the pure polymer, or by dilution of these polymers in certain solvents. By virtue of their lyotropic character, these compounds are very suitable for dissolving various coloring agents, ionic or otherwise, the value of which in displays is known. Most current liquid crystals are decomposed by ionic coloring agents under the action of electric fields.

BRIEF DESCRIPTION OF THE DRAWINGS

The infrared spectra (in KBr) of certain derivatives of the invention herein are shown in FIGS. 1 through 4.

The polymers according to the invention result from the polymerization of one or several monomers of formula (I):

$$H_2C=C(R)-C(=O)-Z-B-NH-(AA)_p \quad (I)$$

Figure 1:
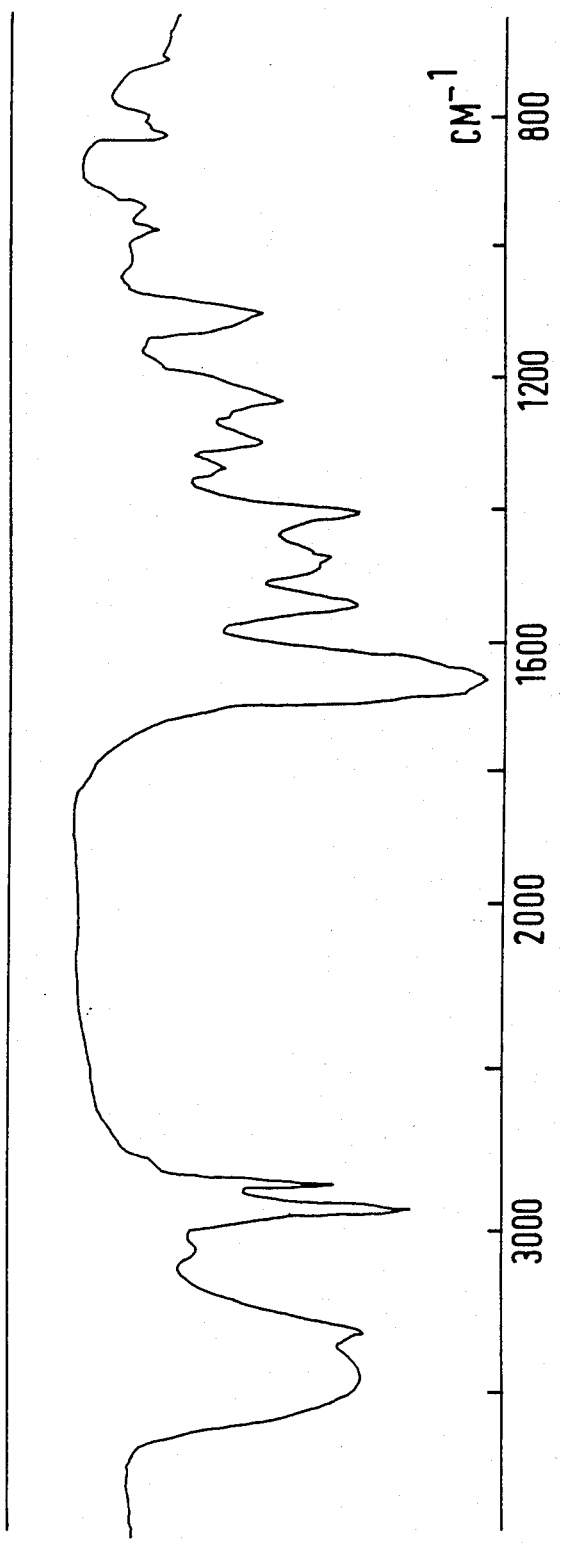

where:
R represents H or a lower alkyl group of $C_1$ to $C_3$;
Z is O or NH;
B has the formula:

$$-(CH_2)_{q1}-Z_1-(CH_2)_{q2}-$$

where $q_1$ and $q_2$ are integers greater than or equal to 1, the sum of which is less than approximately 32, and $Z_1$ represents a single bond or O, S, NH, CO or CO—NH;

$(AA)_p$ represents a peptide radical comprising p coupled aliphatic alpha-amino-acids, bound at B by its carboxyl group, each amino acid comprising less than 15 carbon atoms and being possibly substituted at one carbon atom of the chain by a carboxylic acid or ester, amide or amine group, the terminal amine group of the peptide radical being possibly acylated by a R'CO group, R' being an alkyl radical comprising 1 to 4 carbon atoms, or by any other group stable under the conditions of synthesis; and p represents a number ranging between 1 and 200.

B comprises in particular 6 to 24 carbon atoms.

Mixtures of these polymers and copolymers is another object of the invention. They can comprise compounds of various degrees of polymerization, mixtures resulting from the polymerization reaction of the vinyl group; they can also be mixtures derived from mixtures of monomers obtained from the polymerization reaction of terminal polypeptides, and therefore having different values of p.

In addition, the copolymers resulting from statistical polymerization of monomers of formula (I) with compounds of formula (II):

$$H_2C=C(R)-C(=O)-Z(CH_2)_n-R^o \quad (II)$$

where:
n ranges between 2 and 30;
R and Z have the same meaning as above; and
$R^o$ represents $CH_3$ or OH, are also an object of the invention.

The amino acids from which originates the terminal part of the branched chain of the polymer, represented by $(AA)_p$, have hydrophobic or hydrophilic side chains. This terminal part results from the condensation, by peptide bond, of amino acids between them and at B, such that if B is $(CH_2)_3$— and p=1, —Z—B—NH—$(AA)_p$ means:

$$-HN-(CH_2)_3-NH-\underset{\underset{O}{\|}}{C}-\underset{\underset{NHR_2}{|}}{CH}-(CH_2)_r-Z_2$$

where:
r is an integer ranging between 0 and 5;
$Z_2$ represents an amino group, substituted or otherwise, or a carboxylic acid, ester or amide group; and
$R_2$ represents H or COR',
or further if p=3, —Z—B—NH$(AA)_3$ means:

$$-HN-(CH_2)_3-NH-\underset{\underset{O}{\|}}{C}-CH-(CH_2)_r-Z_2$$
$$| $$
$$NH$$
$$|$$
$$C=O$$
$$|$$
$$CH-(CH_2)_r-Z_2$$
$$|$$
$$NH$$
$$|$$
$$C=O$$
$$|$$
$$CH-(CH_2)_r-Z_2$$
$$|$$
$$NHR_2$$

where:
r and $Z_2$ have the same meanings as above; and $R_2$ represents H or $-COR'$, $R'$ being an alkyl group of $C_1$, to $C_4$.

The preferred amino acids are shown below in table I:

TABLE I

| Abbreviation | Structural formula | Usual name of amino acid |
|---|---|---|
| Sar | HN—CH$_2$—COOH<br>\|<br>CH$_3$ | Sarcosine |
| Orn | H$_2$N—CH—COOH<br>\|<br>(CH$_2$)$_3$—NH$_2$ | Ornithine |
| K | H$_2$N—CH—COOH<br>\|<br>(CH$_2$)$_4$—NH$_2$ | Lysine |
| E | H$_2$N—CH—COOH<br>\|<br>(CH$_2$)$_2$—COOH | Glutamic acid |
| D | H$_2$N—CH—COOH<br>\|<br>CH$_2$—COOH | Aspartic acid |
| EnEt | H$_2$N—CH—COOH<br>\|<br>(CH$_2$)$_2$—CO—NH—(CH$_2$)$_2$—OH | Hydroxyethylglutamine |
| EnPro | H$_2$N—CH—COOH<br>\|<br>(CH$_2$)$_2$—CO—NH—(CH$_2$)$_3$OH | Hydroxypropylglutamine |
| EnBu | H$_2$N—CH—COOH<br>\|<br>(CH$_2$)$_2$—CO—NH—(CH$_2$)$_4$OH | Hydroxybutylglutamine |
| EnPen | H$_2$N—CH—COOH<br>\|<br>(CH$_2$)$_2$—CO—NH—(CH$_2$)$_5$OH | Hydroxypentylglutamine |
| DnEt | H$_2$N—CH—COOH<br>\|<br>CH$_2$—CO—NH—(CH$_2$)$_2$OH | Hydroxyethylaspartamine |
| Ebzl | H$_2$N—CH—COOH<br>\|<br>(CH$_2$)$_2$—COO—CH$_2$—C$_6$H$_5$ | Benzyl glutamate |
| Dbzl | H$_2$N—CH—COOH<br>\|<br>CH$_2$—COO—CH$_2$—C$_6$H$_5$ | Benzyl aspartate |
| KTfa | H$_2$N—CH—COOH<br>\|<br>(CH$_2$)$_4$—NH—CO—CF$_3$ | Trifluoroacetyllysine |
| OrnTfa | H$_2$N—CH—COOH<br>\|<br>(CH$_2$)$_3$—NH—CO—CF$_3$ | Trifluoroacetylornithine |
| KCbz | H$_2$N—CH—COOH<br>\|<br>(CH$_2$)$_4$—NH—COO—CH$_2$—C$_6$H$_5$ | Carbobenzoxylysine |
| OrnCbz | H$_2$N—CH—COOH<br>\|<br>(CH$_2$)$_3$—NH—COO—CH$_2$—C$_6$H$_5$ | Carbobenzoxyornithine |
| EMe | H$_2$N—CH—COOH<br>\|<br>(CH$_2$)$_2$—COOCH$_3$ | Methyl glutamate |

TABLE I-continued

| Abbreviation | Structural formula | Usual name of amino acid |
|---|---|---|
| EEt | H$_2$N—CH—COOH<br>        |<br>   (CH$_2$)$_2$COO—C$_2$H$_5$ | Ethyl glutamate |
| Gly | H$_2$N—CH$_2$—COOH | Glycine |

Amino acids with hydrophobic side chains are used preferably in the form of copolymers with acrylate or acrylamide monomers, given the difficulties of synthesis.

For amino acids with hydrophilic side chain, particularly preferred are sarcosine (Sar), hydroxyethylglutamine (EnEt) and hydroxyethylaspartamine (DnEt); among the amino acids with hydrophobic side chain are preferred trifluoroacetyllysine (KTfa), carbobenzoxylysine (KCbz), alkyl glutamates and benzyl glutamate (Ebzl).

It is also possible to have as terminal group, a polypeptide resulting from the coupling of different amino acids; nevertheless, it is preferable that they are identical, or at least of similar structure, so that the helix of the polypeptide with hydrophobic side chain is not destabilized and the formation of liquid crystals, hindered.

For amino acids with hydrophilic side chain, p<60 is preferred, while p<200 is preferred for those with hydrophobic side chain.

Monomers of formula I can be prepared depending on the type of amino acid and the value of p:

(a) either by first reacting a polymerizable molecule:

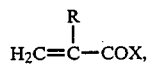

where COX represents a reactive derivative of carboxylic acid, such as an ester, acid chloride, anhydride or others, with a compound of formula HZ—B—NH$_2$ in which Z and B have the meanings indicated above, or with one of its derivatives in which the amine group is temporarily blocked to give a product of formula:

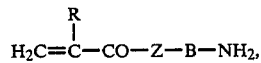

to which is bound, the group(s) derived from amino acids, by reacting, either the N-carboxyanhydride of the alpha-amino acid, or, under the conditions of peptide synthesis, an alpha-amino acid the alpha amine group of which is protected, for example, by the t-butyloxycarbonyl group; in all cases, the other possible reactive groups are protected in a conventional way.

(b) either by reacting the polymerizable molecule:

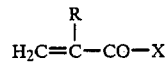

where CO—X has the same meaning as in the previous paragraph (a) on the amine group of a long-chain amino acid:

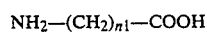

with $n_1$ representing an integer from 2 to 11, then by activating the acid group of the derivative obtained in the from of a succinimidyl ester, and lastly reacting the activated ester with a diamine:

with $n_2$=an integer ranging between 2 and 20 to obtain the polymerizable amine:

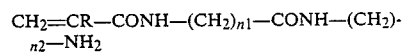

to which can be bound the group(s) derived from amino acids as described in (a).

(c) or by reacting the polymerizable molecule previously mentioned:

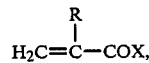

with a compound of formula HZ—B—(AA)$_p$, in wich Z, B, AA and p have the same meanings as before and for which the amine group of the last AA is blocked, or a mixture of these compounds which have identical Z, B, and AA, but different values of p.

The conditions of these various reactions are well known to those skilled in the art.

In the process according to (a), one of the amine groups of the diamine of formula H$_2$N—B—NH$_2$ or the amine group of the amino alcohol HO—B—NH$_2$ will be blocked by a protective group, such as t-butyloxycarbonyl, trifluoroacetyl, 2-nitrophenylsulfonyl or 9-fluorenylmethyloxycarbonyl groups, by methods known in themselves.

In one or other of processes (a) and (b), the preferred method involves N-carboxyanhydride (NCA) for values of p greater than approximately 5 up to 200; the peptide coupling method virtually only gives low values of p, of 4 at most, and, in this case, it is possible either to react the amino acid to be bound, the amine group of which is protected, with the polymerizable amine, and repeat the operation to couple several amino acids, or directly react the di- or tripeptide the terminal amine group of which has been protected.

In the process according to (c), to prepare the compound of formula HZ—B—(AA)$_p$, the N-carboxyanhydride of an amino acid is reacted with the amine HZ—B—NH$_2$, after having protected ZH is a conventional way when Z represents NH. The free amine group of the polypeptide, which is bound, for example, by the action of R'COCl on the product obtained in solution in THF and in the presence of triethylamine, is then blocked; other groups can be introduced if they are stable in the later steps of the syntheses and are not voluminous. This method is particularly useful when AA represents KTfa, OrnTfa, Ebzl and Dbzl. The conditions for obtaining $HZ—B—(AA)_p$ from the protected derivative differ according to the nature of AA; if AA is Sar, KTfa, OrnTfa, Ebzl or Dbzl, the protective group BOC is eliminated, by action of anhydrous HCl in solution in THF; to obtain compounds where AA is K and Orn, piperidine is then reacted with derivatives where AA is KTfa and OrnTfa in solution in THF, or these derived products are treated with NaOH in aqueous and then methanol solution; if AA is Ebzl or Dbzl, it is preferable to block the amine group beforehand with a 2-nitrophenylsulfonyl group rather than with BOC, which can be eliminated after coupling of the amino acids, in slightly acid medium; from these last compounds can be obtained those in which AA is E and D by action of an acid then a base in aqueous medium; finally, in the case of Kbz and OrnCbz, the amine group is blocked preferably, by a trifluoroacetyl or 9-fluorenylmethyloxycarbonyl group which can be eliminated in basic medium, without hydrolysis of Cbz groups. In the case of other amino acids with "sensitive" groups, those skilled in the art will be able to determine which protective group to choose for the amine group, so that its elimination has no effect on the bound polypeptide.

Polymerization of the acrylic group is carried out in a conventional way, in aqueous solution with potassium persulfate as initiator for monomers soluble in water at neutral or basic pH, or in organic solution in THF or chlorofrom, with a peroxide or azobisisobutyronitrile as initiator; it is possible to copolymerize various monomers of formula (I), or a monomer of formula (I) with an alkyl or hydroxylalkyl acrylate of formula:

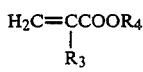

or an acrylamide of formula:

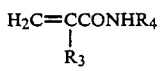

where:

$R_3$ represents hydrogen or a lower alkyl group of $C_1$-$C_3$; and $R_4$ contains 1 to 18 carbon atoms.

The monomers in which AA represents KTfa, OrnTfa, KCbz, OrnCbz, Ebzl, EMe, EEt or Dbzl, that is, amino acids with hydrophobic side chains, copolymerize easily with acrylates and acrylamides in organic solution, whereas in the case of AA groups such as Sar, K, Orn, D and E, it is possible to operate in aqueous solution if the comonomer is soluble. The polymers which generally occur in the form of white powder, are isolated by precipitation, possibly after purification, for example, by dialysis, or from organic solutions by distillation.

Studies by X-ray diffraction, polarizing microscopy and differential enthalpic analysis of branched polymers, both in the dry state and in solution in various solvents, have established the thermotropic and lyotropic character of these compounds.

Differential enthalpic analysis has established the stability domain for the different liquid crystal phases. X-ray diffraction has established the structure of the different liquid crystal phases (various types of smectic, nematic, cholesteric) and has linked the structures of liquid crystal phases to the type of AA amino acids, to their degree of polymerization p and to the lenght of the spacer arm B.

The use of these compounds in applications resulting from their liquid crystal structures is conventional, and is known to those skilled in the art.

Branched polymers prepared from amino acids with hydrophilic side chains such as Sar, K, Orn, E, D, EnEt and DnEt, for which the value of p is less than about 30, and B has a number of carbon atoms ranging between 2 and 24 also have emulsifying and foaming properties. The same is true for polymers prepared by copolymerization of polymerizable lipopeptides (I) (obtained from amino acids with hydrophilic side chains) and alkoyl acrylates or methacrylates, or acryl- or methacrylamides with 12 to 18 carbon atoms in the alkyl chain. The emulsifying and foaming properties of these polymers have been tested with respect to numerous water/hydrocarbon and water systems, basic products in the cosmetic industry. The type and stability of the emulsions obtained have been studied by the method of selective coloring agents, the method of dilutions, electrical conductivity and electron microscopy.

To obtain emulsions, 2 to 10% of comb polymer is added to two non-miscible liquids, the mixture is agitated for 10 to 30 minutes and the emulsion forms easily. Emulsions of various compositions (from 5 to 60% oil) have been prepared in this way with water/octane, water/decane, water/isopropyl myristate, water/isopropyl palmitate, water/butyl or ethyl stearate, water/cosbiol, water/mygliol, water/carnation oil, water/petrolatum oil and water/silicone oil systems. The emulsions obtained are very stable (several months). The viscosity, compactness and dimensions of the emulsions can be changed by varying the branched polymer content (from 2 to 10%), and by adding a co-surfactant (a long-chain alcohol), such as cetyl alcohol, for example).

In addition, it is possible to vary the solubility and HLB (hydrophilic-lipophilic balance) of branched polymers by altering the nature of the AA amino acid and its degree of polymerization p, the length of the spacer arm B, the type of polymeric backbone (acrylate, methacrylate, acrylamide, methacrylamide) and the lipopeptide and long-chain acrylate, methacrylate, acrylamide or methacrylamide composition of the branched polypeptide.

Branched polymers, in particular in the form of copolymers of lipopeptides (obtained from amino acids with hydrophilic side chains) and acrylates, methacrylates, acrylamides and methacrylamides with long alkyl chains (from $C_{12}$ to $C_{18}$) possess excellent emulsifying and foaming properties and can be used in the cosmetic and dermatologic industry (moisturizing creams, anti-wrinkle creams, varnishes, shampoos, etc) or in the petroleum industry (lubricants, additives, etc.) In addition to their surfactant properties, branched polymers are stable, chemically inert, etc.

The present invention is illustrated by the following examples. In the examples illustrating the preparation of polymers (i.e. from example 3), the values of p indicated are the average degrees of polymerization in number.

EXAMPLE 1

Preparations of compound of formula:

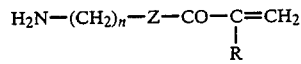

with:
n=3, 5, 6 or 12;
R=H or CH₃; and
Z=O or NH.

(a) —0.1 mole of di-t-butyl CO(OC₄H₉)₂ is reacted at room temperature with 0.1 mole of diamine or aminoalcohol (H₂N(CH₂)$_n$NH₂ or H₂N(CH₂)$_n$OH) in solution in 300 ml of a water/methanol mixture (50/50, v/v) and in the presence of a sufficient quantity of NaOH to maintain a basic pH. After about 12 hours, the final product BOC—NH—(CH₂)$_n$NH₂ (or OH) is precipitated by the addition of water and purified.

For Z=NH and n=12, the final product is separated from the starting product by extraction with tetrahydrofuran, then from the diacyl derivative by chromatography on a silica gel column, with methanol containing 1% NH₄OH as eluent.

For Z=NH and n=6, the diacryl derivative is insoluble in water and the final product is separated from the starting diamine by extraction of the aqueous solution of the mixture with ethyl acetate.

For Z=OH and n=3 or 5, the final product is purified by chromatography on a silica column.

(b) —0.15 mole of acryloyl (or methacryloyl) chloride in solution in 200 ml of THF (tetrahydrofuran) containing 0.15 mole of triethylamine is added dropwise to a solution of 0.1 mole of this product in 300 ml of THF; the precipitate of triethylamine hydrochloride is separated by filtration and the desired product is precipitated by addition of water, then the protective group (BOC) is eliminated by the action of hydrobromic acid on the product in solution in acetic acid or THF (0.1 mole of acyl derivative, in 125 ml acetic acid containing 4M HBr).

After several hours, HBr and CH₃COOH are eliminated by distillation then lyophilization and the residue is dissolved in water.

The salt is decomposed by addition of NaOH and the final products which precipitate are isolated. The purity of the products prepared at each step is confirmed by thin-layer chromatography on silica gel, with CH₃OH+1% NH₄OH as eluent.

The characteristic bands of the infrared spectra (KBr) of the final products are for step (a) at 2920, 2840, 1470 (aliphatic chain) and 1690, 1175 cm⁻¹ (BOC); for step (b) before the elimination of BOC: the same bands as above with 1630 (vinyl), 1660 (amide) and without protective group 2920, 2840, 1470 (aliphatic chain), 1630 (vinyl), 1660 and 1560 (amide).

EXAMPLE 2

Preparation of:

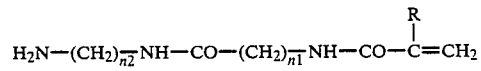

with:
n2=6 to 12;
n1=4 to 11; and
R=H or CH₃.

(a) 12-(acrylolyamino)lauric acid:

12-(acryloylamino)lauric acid is prepared by the method described by W, de Winter and A. Marien (Makromol. Chem. Rapid Commun. 5 (1984) 593–96) for 11-(methacryloylamino)undecanoic acid.

21.5 g (0.1 mole) of 12-aminolauric acid is dissolved in am aqueous solution of sodium hydroxide (0.2 mole), 8.2 ml (0.1 mole) of acryloyl chloride is added dropwise. After neutralization with hydrochloric acid, filtration and recrystallization from ethyl acetate (in the presence of a small amount of 2,6-di-tert-butyl-p-cresol), 19 g of 12-(acryloylamino)lauric acid is obtained (70% yield).

Its IR spectrum is characterized by bands at 1700 cm⁻¹ (acid), 1655, 1535 and 3315 cm⁻¹ (amide) and 1630 cm⁻¹ (CH₂=CH double bond).

A single spot is seen in TLC: R$_f$=0.30 in CHCl₃/MeOH (10/1).

(b) Succinimidyl 12-(acryloylamino)laurate:

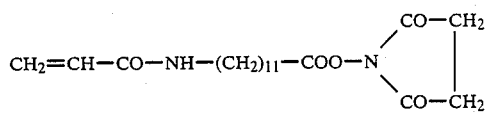

13.45 g (0.05 mole) of 12-(acryloylamino)lauric acid, 6.9 g (0.06 mole) of N-hydroxysuccinimide and a small amount of 2,6-di-tert-butyl-p-cresol are dissolved in 250 ml of THF and the solution is cooled to 0° C. 10.3 g (0.05 mole) of N,N'-dicyclohexylcarbodiimide is added. After 20 hours of reaction, the precipitate of dicyclohexylurea is filtered, the solution is evaporated, the residue is dissolved in 100 ml of acetone and the solution is filtered and evaporated. The residue is redissolved in 30 ml of hot ethanol, is allowed to cool and one volume of water is added under agitation. The mixture is filtered, washed and dried. 16.5 g of ester is recovered (90% yield).

The IR spectrum of the ester is characterized by the disappearance of the acid band at 1700 cm⁻¹ and the presence of bands at 1660, 1540 and 3330 cm⁻¹ (amide), at 1630 cm⁻¹ (acrylic double bond), at 1730, 1745, 1790, 1820, 1210 and 1075 cm⁻¹ (succinimidyl ester).

A single spot is seen in TLC: R$_f$=0.51 in CHCl₃/MeOH (10/1).

(c) N-[12-(acryloylamino)lauryl]1,6-diaminohexane:

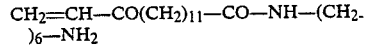

14.6 g (0.04 mole) of the ester prepared in (b) is dissolved in 200 ml of acetone and added slowly with stirring to a solution of 46.4 g (0.4 mole) of 1,6-diaminohexane in 500 ml of an acetone/water mixture (1/1). 2 l of water is added and the precipitate formed is filtered and washed with water. The precipitate is dissolved in 500 ml of an acetone/0.2N aqueous HCl mixture (1/1 in vol.), filtered if necessary and precipitated by addition of 2 l of 0.05N sodium hydroxide. The precipitate is filtered, washed and dried, 12.5 g of amine product is recovered (85% yield).

The IR spectrum of the product is characterized by the disappearance of all the succinimidyl ester bands and the appearance of an additional amide band at 1640 cm⁻¹.

A single spot is seen in TLC: $R_f=0.3$ in 99% ethanol, 1% acetic acid, development is carried out by ninhydrin for the amine and by an aqueous solution of 1.6% $NaIO_4$, 0.2% $KMnO_4$ and 0.4% $Na_2CO_3$ for the double bond.

The determination of the terminal amine group by perchloric acid in acetic acid gives a value of 1.

EXAMPLE 3

Binding of the polypeptide.

A. N-carboxyanhydride method (NCA)

1—Preparation of the compound of formula:

$$CH_2=CH-CO-NH-(CH_2)_{12}-NH-(Sar)_{6.5}$$

0.06 mole of sarcosine N-carboxyanhydride prepared by the action of phosgene on the amino acid, is reacted with 0.01 mole of the polymerizable amine $$CH_2=CH-CO-NH-(CH_2)_{12}NH_2$$

prepared as for example 1 in solution in 250 ml of tetrahydrofuran (THF), at room temperature, under agitation, for one hour.

The solvent is then evaporated and the residue washed by ice-cold acetone and dissolved in water before lyophilization.

The average number of amino acid residues coupled to the polymerizable amine is determined by measuring the terminal amine group by $HClO_4$ in $CH_3COOH$. Under these conditions, an average value for p of 6.5 has been measured; the IR spectrum of the prepared product of formula:

$$CH_2=CHCONH(CH_2)_{12}NH(Sar)_{6.5}$$

is shown in FIG. 1.

2—Preparaton of the compound of formula:

$$CH_2=CH-CO-NH-(CH_2)_{12}-NH-(Sar)_{30}$$

theoretical value of p=30; measured values of p=43, 34 and 21.

0.3 mole of sarcosine N-carboxyanhydride is then transferred into a solution of 0.01 mole of polymerizable amine:

$$CH_2=CHCONH(CH_2)_{12}NH_2$$

in solution in 800 ml of THF and 200 ml of methanol. After one hour of agitation at room temperature, the final mixture of products is isolated as previously.

The final mixture was dissolved in methanol and by addition of acetone, and a yield of 81% with respect to gross weight was obtained for three successive precipitates weighing 1.5 g, 1.3 g and 5 g for which the values of p were respectively 42, 34 and 21.

3—Preparation of the compound of formula:

$$CH_3$$
$$|$$
$$CH_2=C-CO-NH-(CH_2)_{12}-NH-(Sar)_{8.8}$$

By reacting only 0.1 mole of sarcosine N-carboxyanhydride with the amine $$CH_3$$
$$|$$
$$CH_2=C-CO-NH-(CH_2)_{12}-NH_2$$

in solution in 200 ml of THF and 50 ml of methanol, a lipopeptide is obtained of degree of polymerization, determined by measurement of the terminal amine group, of p=8.8

4—Preparation of the compound of formula:

$$CH_2=CH-CO-NH-(CH_2)_6-NH-(Sar)_{5.2}$$

0.05 mole of sarcosine N-carboxyanhydride is reacted with 0.01 mole of polymerizable amine $$CH_2=CH-CO-NH-(C_2)_6NH_2$$

in solution in 250 ml of THF, at room temperature, under agitation, for one hour.

The polymerizable lipopeptide is recovered by evaporation of the solvent, dissolution in water and lyophilization. Determination of the terminal amine group gives p=5.2.

5—Preparation of compound of formula:

$$CH_3$$
$$|$$
$$CH_2=C-COO-(CH_2)_5-NH-(Sar)_{12}$$

0.15 mole of sarcosine N-carboxyanhydride is reacted with 0.01 mole of polymerizable amine $$CH_3$$
$$|$$
$$CH_2=C-CO-(CH_2)_5NH_2$$

in solution in 200 ml of THF and 50 ml of methanol, at room temperature, under agitation, for one hour. The solution is concentrated and the polymerizable lipopeptide is recovered by precipitation with ether. Determination of the terminal amine group gives p=12.

6—Preparation of the compound of formula:

$$CH_2=CH-CO-NH-(CH_2)_{11}-CO-NH-(CH_2)_6-NH-(Sar)_6$$

0.07 mole of sarcosine N-carboxyanhydride is reacted with 0.01 mole of polymerizable amine $$CH_2=CH-CO-NH-(CH_2)_{11}-CO-NH-(CH_2)_6NH_2$$

in solution in 200 ml of THF and 100 ml of methanol, at room temperature, under agitation, for one hour. The mixture is concentrated by rotary evaporation and the polymerizable lipopeptide is precipitated by ethyl ether. Determination of the terminal amine group gives p=6.

7—Preparation of the compound of formula:

$$CH_2=CH-CO-NH-(CH_2)_{12}-NH-(KCbz)_{18}$$

0.2 mol of carbobenzoxylysine N-carboxyanhydride is reacted with 0.01 mole of polymerizable amine $$CH_2=CH-CO-NH-(CH_2)_{12}-NH_2$$

in solution in 500 ml of THF, at room temperature, under agitation, for 12 hours. The polymerizable lipopeptide is precipitated by methanol. Determination of the terminal amine group gives p=18.

8—Preparation of the compound of formula:

$$CH_2=CH-CO-NH-(CH_2)_{12}-NH-(KTfa)_{4.8}$$

0.04 mole of trifluoroacetyllysine N-carboxyanhydride is reacted with 0.01 mole of polymerizable amine $$CH_2=CH-CO-NH-(CH_2)_{12}NH_2$$

in solution in 200 ml of THF, at room temperature, under agitation, for six hours. The polymerizable lipopeptide is precipitated by water. Determination of the terminal amine group gives p=4.8.

9—Preparation of the compound of formula:

$$CH_2=CH-CO-NH-(CH_2)_{12}-NH-(K)_{4.8}$$

0.01 mole of lipopeptide $$CH_2=CH-CO-NH-(CH_2)_{12}NH-(KTfa)_{4.8}$$

is dissolved in 250 ml of methanol then treated with 250 ml of a 1K solution of piperidine in water. The reaction is allowed to proceed for 24 hours. The mixture is evaporated, the residue is dissolved in a water/methanol mixture (90/10 v/v), passed through an ion-exchange column (Dowex 1×2) to eliminate trifluoroacetate ions and lyophilized. I.R. spectroscopy is used to verify the disappearance of the strong absorption bands of the trifluoroacetyl group at 1160-1210 cm$^{-1}$.

10—Preparation of the compound of formula:

$$CH_2=CH-CO-NH-(CH_2)_{12}-NH-(Ebzl)_{5.2}$$

0.05 mole of benzyl glutamate N-carboxyanhydride is reacted with 0.01 mole of the polymerizable amine $$CH_2=CH-CO-NH-(CH_2)_{12}NH_2$$

in solution in 500 ml of THF, at room temperature, under agitation for 12 hours. The lipopeptide $$CH_2=CH-CO-NH-(CH_2)_{12}-NH-(Ebzl)_p$$

is recovered by precipitation with water. Determination of the terminal amine group gives p=5.2.

11—Preparation of the compound of formula:

$$CH_2=CH-CO-NH-(CH_2)_{12}-NH-(E)_{5.2}$$

0.01 mole of the lipopeptide $$CH_2=CH-CO-NH-(CH_2)_{12}NH-(Ezl)_{5.2}$$

is dissolved in 100 ml of THF. This is treated with sodium hydroxide in alcohol solution, water is gradually added to give a clear solution of sodium lipoglutamate, which is concentrated and precipitated by acetone. Total unblocking of the glutamic acid side chain is controlled by the disappearance of the UV absorption of the benzene moieties at 258 nm.

12—Preparation of the compound of formula:

$$CH_2=CH-CO-NH-(CH_2)_{12}-NH-(EnEt)_{5.2}$$

0.01 mole of lipopeptide $$CH_2=CH-CO-NH-(CH_2)_{12}NH-(Ebzl)_{5.2}$$

is dissolved in 200 ml of dioxane, 0.1 mole of aminoethanol is added and the mixture is heated to 40° C. and allowed to react under agitation for 8 hours. The polymerizable lipopeptide $$CH_2=CH-CO-NH-(CH_2)_{12}-(NH-(EnEt)_{5.2}$$

is precipitated by acetone. The disappearance of the benzyl groups is controlled by U.V. spectroscopy at 258 nm.

13—Preparation of the compound of formula:

$$CH_2=CH-CO-NH-(CH_2)_{12}-NH-(Dbzl)_{3.8}$$

0.03 mole of benzylaspartate N-carboxyanhydride is reacted with 0.01 mole of the polymerizable amine $$CH_2=CH-CO-NH-(CH_2)_{12}-NH_2$$

in solution in 500 ml of THF, at room temperature, under agitation for 12 hours. The lipopeptide $$CH_2=CH-CO-NH-(CH_2)_{12}-NH-(Dbzl)_p$$

is recovered by precipitation with water. Determination of the terminal amine group gives p=3.8.

14—Preparation of the compound of formula:

$$CH_2=CH-CO-NH-(CH_2)_{12}-NH-(D)_{3.8}$$

0.01 mole of lipopeptide $$CH_2=CH-CO-NH-(CH_2)_{12}-NH-(Dbzl)_{3.8}$$

is dissolved in 100 ml of THF and treated with sodium hydroxide in alcohol solution. Water in gradually added to give a clear solution of sodium lipoaspartate; the solution is concentrated and acetone is added to precipitate the lipopeptide $$CH_2=CH-CO-NH-(CH_2)_{12}-NH-(D)_{3.8}$$

The disappearance of benzyl groups is verified by U.V. spectroscopy at 258 nm.

15—Preparation of the compound of formula:

$$CH_2=CH-CO-NH-(CH_2)_{12}-NH-(KTfa)_{50}$$

theoretical value of p=50; measured values of p=70, 40 and 35.

0.5 mole of trifluoroacetyllysine NCA is added to 0.01 mole of $CH_2=CH-CONH(CH_2)_{12}NH_2$ in solution in 1 l of THF and is left under agitation at room temperature for 24 hours. The final product, a mixture of products of varying degrees of polymerization is precipitated by addition of water. This mixture is fractionated by successive precipitations, by the addition of water to its solution in THF. From 20 g, 4.1 g of product is obtained, with p=70, 9.6 g of p=40 and 2.1 g of p=35.

16—Preparation of the compound of formula:

$$CH_2=CH-CO-NH-(CH_2)_{12}NH-(Ebzl)_{50}$$

theoretical value of p=50; measured values of p=65, 45 and 36.

A mixture of 0.01 mole of $CH_2=CH-CO-NH-(CH_2)_{12}NH_2$ in solution in 1 l of THF and 0.5 mole of benzyl glutamate NCA gives a mixture of products the terminal polypeptide of which has varying degress of polymerization. This mixture fractionated in THF/H$_2$O gives, with a 75% yield, 1.6 g of p=65, 5.6 g of p=45 and 1.8 g of p=36.

B. Method of peptide coupling

1—Preparation of $CH_2=CH-CONH(CH_2)_{12}NH-Sar$:

0.01 mole of $CH_2=CH-CONH(CH_2)_{12}NH_2$, 0.01 mole of t-butyloxycarbonylsarcosine (SarBoc), 0.01 mole of N-hydroxysuccinimide and then 0.01 mole of dicyclohexylcarbodiimide are dissolved in 250 ml of THF. After 24 hours of agitation at room temperature, the dicyclohexylurea precipitate is eliminated and the obtained product is precipitated by addition of one volume of water (yield 95%). The IR spectrum (KBr) of the compound presents the intense bands: 2920, 2840, 1470 (aliphatic chain), 1660, 1555 (amide), 1690, 1175 (BOC), 1630 (vinyl).

The amine group is then unblocked by transferring 20 ml of a solution of HCl in ethyl ether (5N) into the product previously obtained in solution in 50 ml of THF, at 0° C. The hydrochloride of the amine precipitates slowly, after about 24 hours at room temperature. It is isolated by filtration at 0° C., yield 92%. The IR spectrum (KBr) presents the same bands, except at 1690 and 1175 and has, in addition, a band at 2420 cm$^{-1}$.

The amide is then separated from its salt by treating the hydrochloride in solution in 50 ml of methanol with one equivalent of aqueous solution of NaOH (1N). The desired product is precipitated by addition of a large excess of water.

It is then purified by chromatography on a column of silica by eluting with methanol containing 1% NH$_4$OH. IR spectrum (KBr) bands cm$^{-1}$: 2920, 2840, 1470, 1660, 1550, 1630.

Thin-layer chromatography on silica gel:

$R_f=0.58$ (eluent $CH_3OH + 1\%$ $NH_4OH$)

To obtain the product of formula:

$CH_2=CH-CONH(CH_2)_{12}NH-Sar_2$

SarBOC is reacted under the same conditions with the product obtained previously.

2—Preparation of $$CH_2=\overset{\overset{CH_3}{|}}{C}-CO-NH-(CH_2)_{12}-NH-Sar$$

0.01 mole of $$CH_2=\overset{\overset{CH_3}{|}}{C}-CO-NH-(CH_2)_{12}-NH_2$$

0.01 mole of Sar-Boc, 0.01 mole of N-hydroxysuccinimide and then 0.01 mole of dicyclohexylcarbodiimide are dissolved in 250 ml of THF. After 24 hours of agitation at room temperature, the dicyclohexylurea precipitate is eliminated and then the product obtained is precipitated by addition of one volume of water (96% yield). The amine group of the sarcosine is then unblocked by action of HCl, then NaOH as in the previous example. At each step of the synthesis, the products are purified and characterized as in the previous example.

3—Preparation of $CH_2=CH-CO-NH-(CH_2)_{12}-NH-Gly$ 0.01 mole of $CH_2=CH-CO-NH-(CH_2)_{12}-NH_2$ 0.01 mole of t-butyloxycarbonylglycine (Gly-Boc), 0.01 mole of N-hydroxysuccinimide and then 0.01 mole of dicyclohexylcarboiimide are dissolved in 250 ml of THF. After 24 hours of reaction, under agitation, at room temperature, the dicyclohexylurea precipitate is eliminated by filtration, and $CH_2=CH-CO-NH-(CH_2)_{12}-NH-Gly-Boc$ is precipitated by addition of one volume of water (94% yield). The amine group of the glycine is then unblocked by action of HCl then NaOH as in the case of sarcosine (example 3Bl). At each step of the synthesis, the products obtained are purified and characterized as in example 3Bl.

EXAMPLE 4

Preparation of $$(AA)_pNH-(CH_2)_nNH-CO-\underset{\underset{R}{|}}{C}=CH_2$$

by the intermediate of $(AA)_pNH-(CH_2)_nNH_2$

A. $R_1HN-(CH_2)_2-NH-(AA)p$ with $R_1$=protecting group (BOC, Nps . . . )

(1) n=12, AA=(Sar); p=12.5

0.15 mole of sarcosine NCA is transferred into 200 ml of THF containing 0.01 mole of BOC-NH-(CH$_2$)$_{12}$NH$_2$ and agitated at room temperature for one hour. The final product is isolated by precipitation with acetone. The determination of the terminal amine group gives p=12.5.

(2) n=12, AA=KTfa, p=20

0.2 mole of KTfa NCA is transferred into 1 liter of THF containing 0.01 mole of Boc-NH-(CH$_2$)$_{12}$-NH$_2$ and is left under agitation, at room temperature, 24 hours. The final product is isolated by precipitation with water.

(3) n=12, AA=Ebzl; p=25

0.25 mole of Ebzl NCA is transferred into 1 liter of THF containing 0.01 mole of Nps-NH-(CH$_2$)$_{12}$-NH$_2$ and is left under agitation, at room temperature, 24 hours. The Nps-NH-(CH$_2$)$_{12}$-NH$_2$ is obtained by action of 2-nitrophenylsulfonyl chloride on the diamine.

The final product is isolated by precipitation with water.

B.
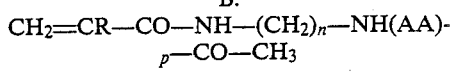

(1) Blocking of the polypeptide: $R_1NH-(CH_2)_n-NH-(AA)_pCOCH_3$.

0.1 mole of the product obtained in A is dissolved in 200 ml to 1000 ml of THF depending on the value of p, with 0.1 mole of triethylamine, then 0.15 mole of acetyl chloride is added and left under agitation at room temperature until a negative reaction is seen with ninhydrin. The precipitate of triethylamine hydrochloride is then eliminated, the solvents are evaporated and an aqueous solution of the residue is lyophilized.

(2) Separation of the amine: $N_2H-(CH_2)_n-NH-(AA)_pCOCH_3$.

If $R_1$=Boc or Nps, the product in solution in THF is treated with anhydrous HCl, and the amine is separated from its salt by methanolic NaOH.

(3) Acylation:

(a) n=12, AA=Sar.

A solution is prepared of 0.01 mole of amine

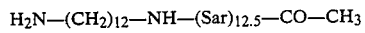

in 200 ml of THF and 20 ml of methanol. Acryloyl chloride and its triethylamine equivalent (TEA) both in solution in THF (a few ml) are added slowly and simultaneously. The reaction is stopped when the ninhydrin reaction becomes negative i.e. for about 0.013 mole. The solution is evaporated, the residue dissolved in water, passed through an ion-exchange column (OH⁻ form) and lyophilized. The product obtained is dissolved in a small volume of methanol and precipitated by diethyl ether. This is filtered, washed and dried to recover the lipopeptide

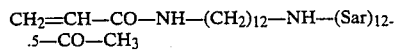

To obtain

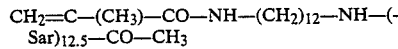

an identical method is used, but acryloyl chloride is replaced by methacryloyl chloride. In both cases, the yield is 95%.

(b) n=12, AA=KTfa

A solution is prepared of 0.01 mole of amine

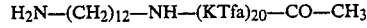

in 200 ml of THF. Acryloyl chloride and its TEA equivalent both in solution in THF are added slowly and simultaneously. The reaction is stopped when the ninhydrin test becomes negative, i.e. for about 0.015 mole. The TEA hydrochloride is filtered and water is used to precipitate the lipopeptide

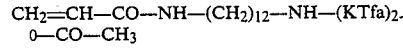

(c) n=12; AA=Ebzl

The starting compound is the amine

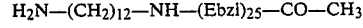

and under the same conditions as in the previous example the following polypeptide is obtained

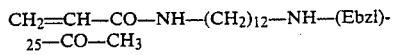

EXAMPLE 5

Polymerization.

A. In aqueous medium 0.01 mole of

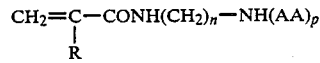

$5\times10^{-4}$ mole of potassium persulfate and 140 μl of N,N,N',N'-tetramethylethylenediamine in 350 ml of water is left, under agitation, for 48 hours. The polymer is isolated by lyophilization, then purified by dialysis.

(1) In this way, starting from the product isolated in example 3A1, i.e.

Figure 2:
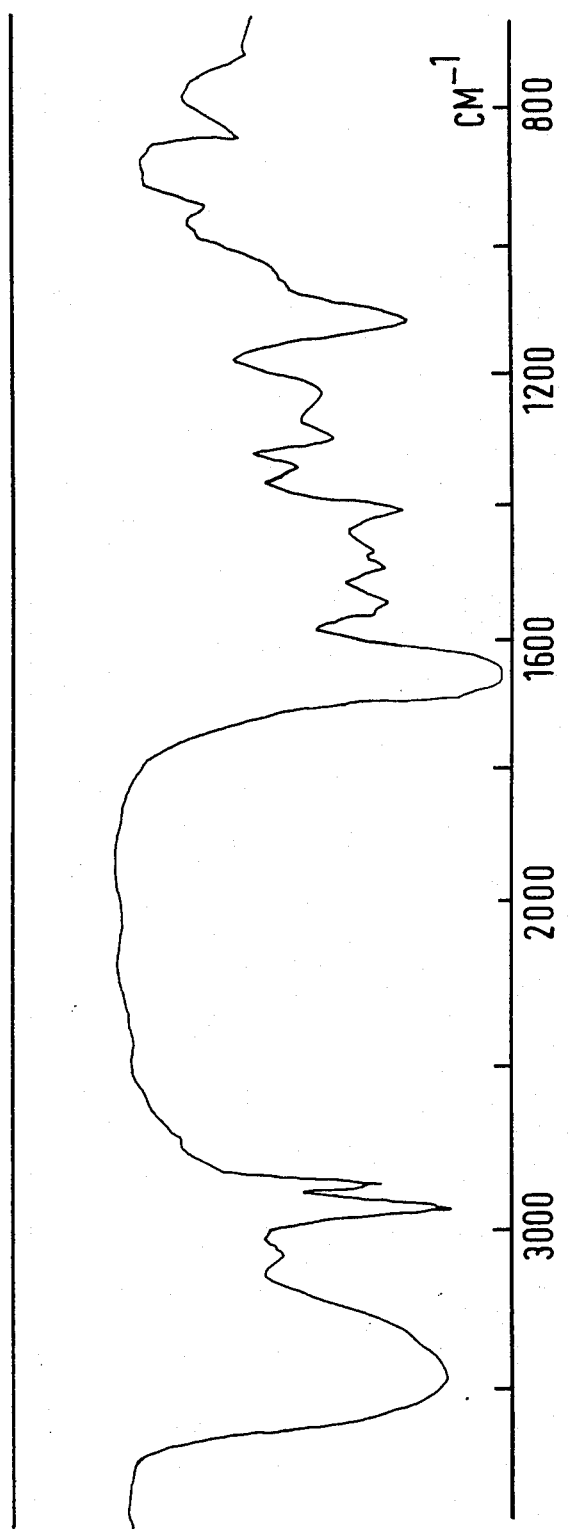

a compound is obtained with a specific viscosity in water of 0.25 dlg⁻¹ and which forms a smectic mesophase at room temperature and is transformed into nematic at 90° C., isotropization occurs at a temperature greater than 180° C. This polymer is also lyotropic: at room temperature, the smectic/nematic transition occurs for 23% water, whereas isotropization occurs for about 50%. Its IR (KBr) spectrum is shown in FIG. 2.

(2) From the lipopeptide

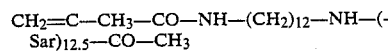

isolated in example 4Ba, is obtained a comb polymer which forms a smectic mesophase between room temperature and 120° C.; in addition, this polymer is lyotropic and its smectic phase exists at room temperature for water contents between 0 and 30%.

B. Polymerization in organic solvent:

A solution (of polymerizable lipopeptide and possibly comonomer) in THF, chloroform or a mixture of THF/chloroform, of concentration from 2 to 5% by weight and containing $5\times10^{-4}$ mole of azobisisobutyronitrile for 0.1 mole of monomer is maintained at 60° C. for 48 hours. The branched polymer is precipitated by addition of a large volume of water and is dried.

(1) The product resulting from the polymerization in 100 ml of a THF/chloroform mixture (50/50 v:v) of 0.01 mole of:

obtained in example 3B1, is smectic at room temperature and is transformed to nematic at about 60° C. This polymer is also lyotropic; at room temperature, the smectic-nematic transition occurs for 35% water, whereas isotropization occurs for about 50% water.

(2) The product resulting from the copolymerization in 200 ml of chloroform of 0.01 mole of

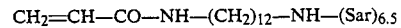

and of 0.025 mole of tetradecylacrylamide:

$$CH_2=CH-CO-NH-(CH_2)_{14}-H$$

gives a comb copolymer recovered by precipitation with water and for which the determination of the amine groups by perchloric acid and in solution in acetic acid confirms the composition 1/2.5 in mole. This comb copolymer is an excellent emulsifying agent for basic products of the cosmetic industry.

Figure 3:
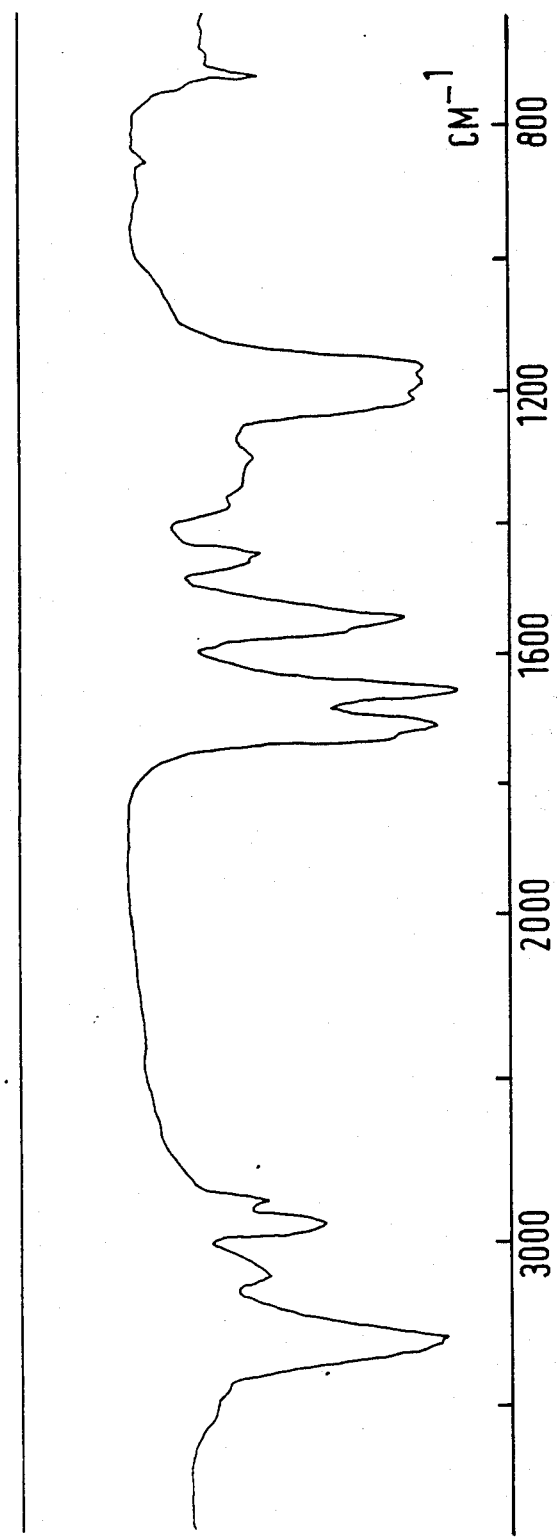

(3) The product resulting from the copolymerization of 0.01 mole of $$CH_2=CHCONH-(CH_2)_{12}-NH(KTfa)_{40}$$

and of 0.04 mole of $$N-(C_{14}H_{28})$$

acrylamide in one liter of THF in the presence of $5 \times 10^{-4}$ mole of azobisisobutyronitrile is nematic at room temperature as is, or in solution in ethyl acetate or dioxane at concentrations less than about 40%; in methanol, it is nematic, then, cholesteric. Its IR spectrum (film) is shown in FIG. 3. Its specific viscosity, measured in dichloroacetic acid, is 0.27 dlg$^{-1}$ at 25° C.

(4) 0.01 mole of copolymer obtained as in the previous example is dissolved in methanol and then treated with NaOH in aqueous solution. This is evaporated, the residue is dissolved in water containing 10% methanol, passed through an anion-exchange column to eliminate trifluoroacetic ions ans then lyophilized. IR spectroscopy is used to verify the disappearance of the strong absorption bands of the trifluoroacetyl group at 1160–1210 cm$^{-1}$.

Figure 4:
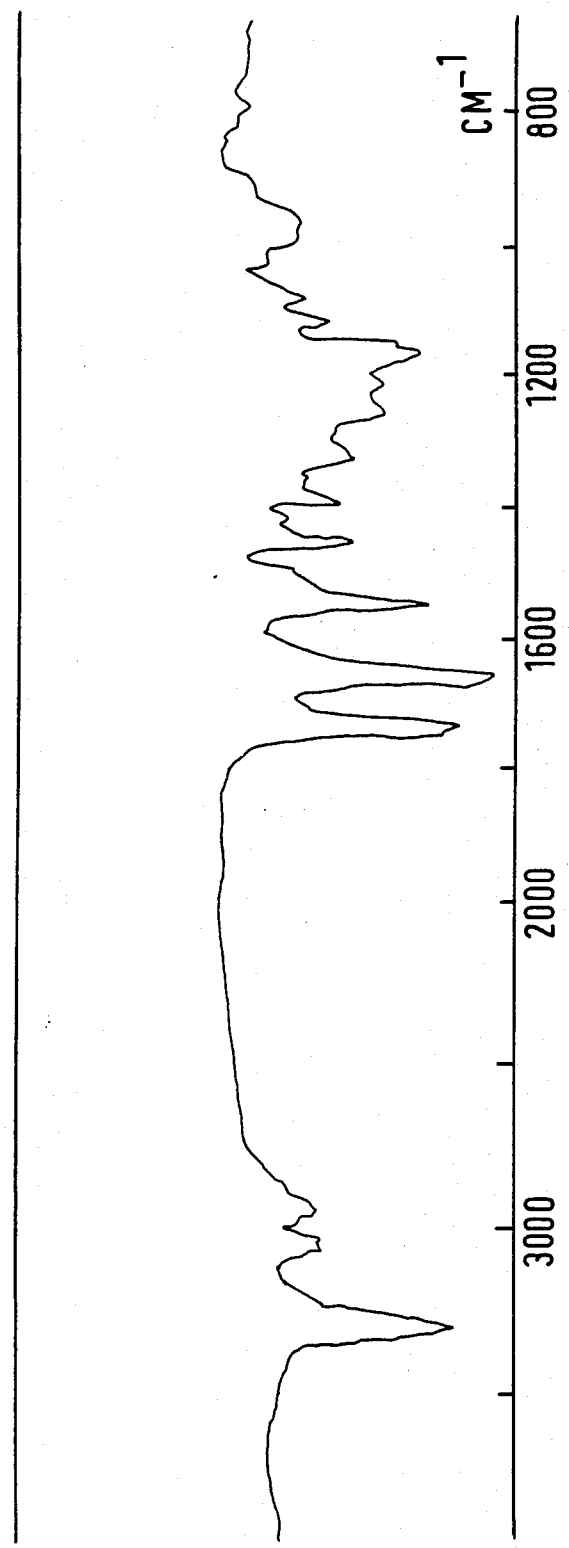

(5) The product resulting from the copolymerization of 0.01 mole of $$CH_2=CH-CO-NH-(CH_2)_{12}-NH-(Ebzl)_{45}$$

and of 0.05 mole of N-tetradecylacrylamide in 1 l of THF in the presence of $5 \times 10^{-4}$ mole of AIBN, has a specific viscosity in dichloroacetic acid of 0.30 dlg$^{-1}$ at 25° C. It is nematic when dry and in dioxane. Its IR spectrum (film) is shown in FIG. 4.

(6) 0.01 mole of the copolymer obtained as in the previous example is dissolved in THF. This is treated with a solution of sodium hydroxide in alcohol, and water is gradually added to give a clear solution, this is concentrated and precipitated with acetone. Total unblocking of the glutamic acid side chain is controlled by the disappearance from the UV absorption spectrum of benzene rings at 258 nm.

(7) 0.01 mole of $$CH_2=CH-CO-NH-(CH_2)_{12}-NH-(KCbz)_{18}$$

and 0.03 mole of N-tetradecylacrylamide are copolymerized at 60° C. in solution in 1 l of THF by $5 \times 10^{-4}$ mole of AIBN. The copolymer obtained is precipitated by methanol, dissolved in acetic acid and lyophilized. At room temperature, it is nematic in the dry state and in solution in dioxane for solvent concentrations of less than about 40%.

(8) The copolymer obtained as in the precious example is dissolved in acetic acid and then treated with 3M HBr in acetic acid. The precipitate of the copolymer (in the form of the bromohydrate) is filtered washed with acetone and dried. The absence of absorption at 258 nm due to benzene rings in verified by UV spectroscopy.

Other polymerizations are carried out in the same way, the results for which are given in Tables II and III below.

TABLE II

Other examples of polymerization of lipopeptides
$CH_2=CR-CO-Z-(CH_2)_n-NH-(AA)_p$

| AA | R | Z | n | p | Solvent | Initiator |
|---|---|---|---|---|---|---|
| Sar | CH$_3$ | NH | 12 | 1 | CHCl$_3$/THF | AIBN |
| | CH$_3$ | NH | 12 | 8.8 | water | Persulfate |
| | H | NH | 12 | 12.5 | water | Persulfate |
| | H | NH | 12 | 21 | water | Persulfate |
| | H | NH | 12 | 34 | water | Persulfate |
| | H | NH | 12 | 42 | water | Persulfate |
| | H | NH | 6 | 5.2 | water | Persulfate |
| | CH$_3$ | O | 5 | 12 | water | Persulfate |
| K | H | NH | 12 | 4.8 | THF | AIBN |
| E | H | NH | 12 | 5.2 | water | Persulfate |
| EnEt | H | NH | 12 | 5.2 | THF | AIBN |
| D | H | NH | 12 | 3.8 | water | Persulfate |

These homopolymers were found to present liquid crystal properties.

TABLE III

Other examples of copolymerization of
$CH_2=CR-CO-Z-(CH_2)_n-NH-(AA)_p$ (I)
with $CH_2=CR'-CO-Z'-(CH_2)_{n'}H$ (II)

| AA | R | Z | n | p | R' | Z' | n' | I/II in moles |
|---|---|---|---|---|---|---|---|---|
| Sar | H | NH | 12 | 6.5 | H | NH | 14 | 1/1.6 |
| | CH$_3$ | NH | 12 | 8.8 | CH$_3$ | NH | 18 | 1/2 |
| | CH$_3$ | NH | 12 | 8.8 | CH$_3$ | NH | 18 | 1/3 |
| | CH$_3$ | NH | 12 | 8.8 | CH$_3$ | NH | 18 | 2/1 |
| | CH$_3$ | O | 5 | 12 | CH$_3$ | 0 | 16 | 1/3 |
| K | H | NH | 12 | 4.8 | H | NH | 18 | 1/3 |
| E | H | NH | 12 | 5.2 | H | NH | 12 | 1/3 |
| EnEt | H | NH | 12 | 5.2 | H | NH | 16 | 1/2 |

All copolymerizations are carried out in solution in THF using AIBN as initiator.

These copolymers were found to present good emulsifying and foaming properties.

We claim:

1. Polymers selected from the group consisting of:
A. homopolymers of monomers having the formula:

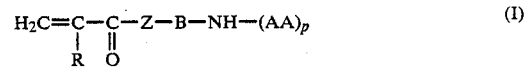

where:

R is H or a lower alkyl group of C$_1$ to C$_3$;

Z is O or NH;

B represents an alkyl chain of C$_2$ to C$_{24}$; and (AA)$_p$ represents a peptide radical comprising p coupled aliphatic amino acids, and bound to B by the carboxyl group of the first amino acid, each amino acid comprising less than 15 carbon atoms and being unsubstituted or substituted at a carbon of the chain by an acid or carboxylic ester, amide or amine group, the terminal amine group being unsubstituted or acylated by a R'CO group, R' being an alkyl radical comprising 1 to 4 carbon atoms, or by a group stable under the condition of the synthesis; AA being derived from amino acids with a hydrophilic side chain; and p is less than 30;

B. copolymers of the monomers of formula I with an alkyl acrylate of the formula:

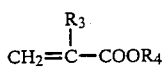

or with an acrylamide of the formula:

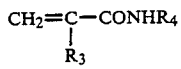

where:

$R_3$ is H or a lower alkyl group of $C_1$ to $C_3$; and $R_4$ represents alkyl or hydroxyalkyl groups of $C_1$ to $C_{18}$;

and mixtures thereof.

2. Polymers according to claim 1, characterized in that they are homopolymers and that AA is the derivative of sarcosine, or hydroxyethylglutamine or of hydroxyethylaspartamine.

3. Polymers according to claim 2, characterized in that AA is the derivative of sarcosine.

4. Polymers according to claim 1, characterized in that they are copolymers and that AA represents an amino acid derivative selected from the group consisting of sarcosine, lysine, ornithine, glutamic acid, aspartic acid, hydroxyethylglutamine and hydroxyethylaspartamine.

5. Polymers according to claim 4, characterized in that AA is the derivative of sarcosine.

6. Polymers according to any one of claims 1 and 2 to 5, characterized in that they result from the copolymerization of at least two monomers of formula (I).

7. Compositions of polymers according to any one of claims 1 and 2 to 5, characterized in that they are mixtures of polymers of different degrees of polymerization, or of different values of p.

8. Emulsifying and foaming agents comprising polymers according to any one of claims 1 and 2 to 5.

* * * * *